United States Patent [19]

Meyer

[11] 3,983,160
[45] Sept. 28, 1976

[54] PROCESS FOR THE PREPARATION OF HYDROXYPHENYLACETONITRILES

[75] Inventor: Horst Meyer, Wuppertal, Germany

[73] Assignee: Bayer Aktiengesellschaft, Germany

[22] Filed: Nov. 20, 1975

[21] Appl. No.: 633,683

[30] Foreign Application Priority Data
Dec. 3, 1974 Germany............................ 2457080

[52] U.S. Cl. ........................ 260/465 F; 260/465 D;
260/471 R
[51] Int. Cl.²...................................... C07C 121/75
[58] Field of Search ..................... 260/465 F, 465 D

[56] References Cited
OTHER PUBLICATIONS
Berlin et al., Chemical Abstracts, vol. 44, pp. 1058–1060 (1950).

*Primary Examiner*—Lewis Gotts
*Assistant Examiner*—Dolph H. Torrence

[57] ABSTRACT

Hydroxyphenylacetonitriles, which are known chemical intermediates, are prepared by the reaction of hydroxybenzyl alcohols and hydrogen cyanide. A representative example is the preparation of 3-methoxy-4-hydroxyphenylacetonitrile from 3-methoxy-4-hydroxybenzyl alcohol and hydrogen cyanide.

13 Claims, No Drawings

PROCESS FOR THE PREPARATION OF HYDROXYPHENYLACETONITRILES

The present invention relates to a new process for the preparation of hydroxyphenylacetonitriles, which are intermediates in the preparation of pharmaceuticals and scents.

Hitherto, phenylacetonitriles have been prepared from benzyl halides which are accessible from benzyl alcohols. These halides are reacted with alkali metal cyanides to give the corresponding phenylacetonitriles. This convenient and standard method however fails in the case of hydroxybenzyl alcohols, since, in converting the benzyl alcohol to the benzyl halide, resinous products (such as phenol-formaldehyde resins) are formed. Presumably this is the result of alkylation reactions occurring at the nucleus. Thus, the phenolic hydroxy groups must be protected beforehand by acylation, which requires two additional steps, for example:

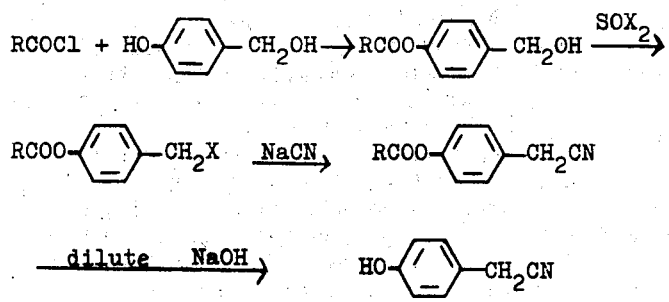

(see, for example, 1) Berlin, Scherlin and Serebrennikowa, Z. obsc. Chim. 19, 759, 766 (1949); CA, Vol. 44, 1058 (1950); and compare H. E. Fisher and H. Hibbert, JACS 69, 1208 (1947)).

One way of circumventing this is the reaction of benzylamines wth alkali metal cyanides, but this reaction provides unsatisfactory yields. Preparation of the starting compounds can also be complicated. See, e.g., J. H. Short, D. A. Dunnigan and C. W. Ours, Tetrahedron 29, 1931 (1973).

Aralkyl cyanides having a phenolic hydroxy group can also be obtained by the reaction of quaternized aralkylamines with sodium methylate, to give aralkyl methyl ethers, followed by nucleophilic exchange with alkali metal cyanide, for example:

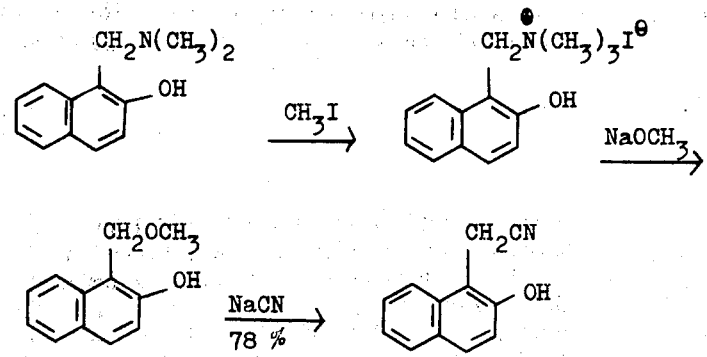

See A. Merijan and P. D. Gardner, Journ. Org. Chem. 30, 3965 (1965).

The good yield in the last reaction step is offset by the many steps and this method does not therefore offer distinct advantages over the previously discussed reaction of protected benzyl alcohols.

The present invention pertains to a process for the preparation of an ortho or parahydroxyphenylacetonitrile of the formula:

wherein
R is ortho or parahydroxyphenyl, further unsubstituted or further substituted by one or two substituents independently selected from the group consisting of lower alkyl or lower alkoxy and
$R^1$ is hydrogen, lower alkyl, phenyl or carbo(lower alkoxy), which comprises allowing the corresponding ortho or parahydroxybenzyl alcohol of the formula:

to react with hydrogen cyanide in the presence of a diluent at a temperature of from about 80° to about 190°C.

The hydroxyphenylacetonitriles of the Formula I includes parahydroxy compounds of the formula:

(IA)

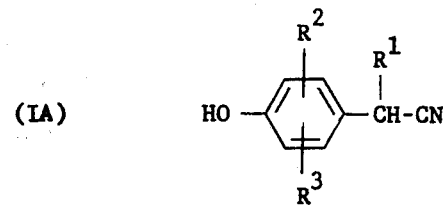

and orthohydroxy compounds of the formula:

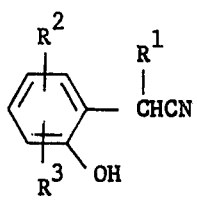

(IB)

in which
R¹ is hydrogen, lower alkyl, phenyl or carbo(lower alkoxy), and
each of R² and R³ is independently hydrogen, lower alkyl and alkoxy.

The term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec-butyl, tert-butyl, pentyl, isopentyl, neopentyl, tert-pentyl, hexyl, and the like.

The term lower alkoxy denotes a straight or branched hydrocarbon chain of 1 to 6 carbon atoms bound to the remainder of the molecule through a divalent oxygen atom as, for example, methoxy, ethoxy, propoxy, isopropoxy, butoxy, isobutoxy, pentoxy and hexoxy.

It is distinctly surprising that the hydroxyphenylacetonitriles of the Formula I can be obtained in a single step and in such good yields in accordance with the present invention, since the direct conversion of an alcohol to the corresponding nitriles, without the intermediate formation of a halo compound, could not be expected from the state of the art.

The process according to the invention has a number of advantages. Thus, the benzyl alcohols of Formula II are easily accessible by reduction of the corresponding carbonyl compounds or by hydroxyformylation of phenols. The end product is obtained in high yield and high purity. With particular reference to the prior art process for the preparation of hydroxyphenylacetonitriles from the corresponding alcohols, the process offers the advantage that three reaction steps are saved, namely:

a. protection of the phenolic OH group by acylation,
b. preparation of the protected benzyl halide and
c. removal of the acyl protective group.

If 4-hydroxy-3-methoxybenzyl alcohol and hydrocyanic acid are used as starting materials, the course of the reaction can be represented by the following equation:

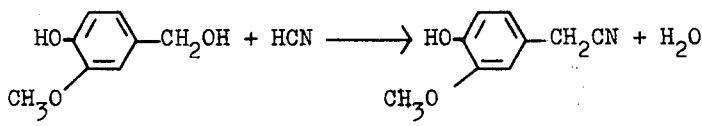

The benzyl alcohols of Formula II are known or can be readily prepared according to known methods, as is discussed above. Examples include 2-hydroxybenzyl alcohol, 4-hydroxybenzyl alcohol, 3-methoxy-4-hydroxybenzyl alcohol, 3-ethoxy-4-hydroxybenzyl alcohol, 2,5-dimethoxy-4-hydroxybenzyl alcohol, 3-methoxy-2-hydroxybenzyl alcohol, 3-methyl-4-hydroxybenzyl alcohol, 1-(4-hydroxyphenyl)-ethanol, 1-(2-hydroxyphenyl)-propanol-1, 4,-hydroxybenzhydrol, 3-butoxy-4-hydroxybenzyl alcohol, 4-hydroxymandelic acid ethyl ester and 3-methoxy-4-hydroxymandelic acid propyl ester.

The hydrocyanic acid can be employed in anhydrous form or, preferably, can be liberated in situ. This can be accomplished by utilizing alkali metal salts or alkaline earth metal cyanides in the presence of an acid as, for example, organic acids such as formic acid or acetic acid. An excess of acid should be avoided. Preferably 1 to 1.5 mols of hydrogen cyanide are employed per mol of benzyl alcohol of Formula II.

The diluents include water and all inert organic solvents, especially polar aprotic solvents, such as N,N-dimethylformamide, dimethylsulfoxide, tetrahydrothiophene-S-dioxide, N-methylpyrrolidone, tetramethylurea, hexamethylphosphoric acid triamide and acetonitrile. Of these, dimethylsulfoxide is preferred.

Temperatures can vary between from about 80° to about 190°C. Preferably, the reaction is carried out at from about 110° to about 140°C.

The reaction can be carried out under normal pressure or under elevated pressure. Preferably, it is carried out at pressures between 1 and 2 atmospheres gauge.

The hydroxyphenylacetonitriles of Formula I are known compounds useful as intermediates in the production of pharmaceuticals and scents. 3-Methoxy-4-hydroxyphenyl acetonitrile, for example, is an intermediate in the preparation of the narcotic propanidid. Thus, according to the known synthetic route, the nitrile is hydrolyzed to yield 3-methoxy-4-hydroxyphenylacetic acid which is esterified to yield the corresponding propyl ester and finally etherified with N,N-diethyl chloroacetamide to yield propyl 3-methoxy-4-(N,N-diethylcarbamylmethoxy)phenylacetate.

The following examples will serve to further typify the nature of this invention but should not be construed as a limitation on the scope thereof.

The process according to the invention may be illustrated by the following examples:

EXAMPLE 1

3-Methoxy-4-hydroxyphenylacetonitrile

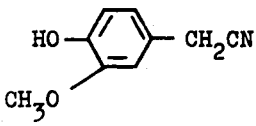

185g of 3-methoxy-4-hydroxybenzyl alcohol and 90g of potassium cyanide are suspended in 1,250 ml of dimethylsulfoxide. 80g of glacial acetic acid are added dropwise at 125°C over the course of 1 hour, while stirring, and the mixture is stirred for a further 2 hours at 125°C. It is then cooled to 90°C and the dimethylsulfoxide is distilled off in a waterpump vacuum. The residue is stirred with 1,200 ml of water and 400 ml of chloroform, the chloroform phase is separated off and the water phase is extracted with a further 400 ml of chloroform. The combined chloroform phases are extracted by shaking with water and dried with sodium sulfate. The chloroform is completely stripped off in vacuo and the residual oil is seeded, whereupon the batch crystallizes throughout. Yield: 172.3g (88% of theory). Melting point: 51°–53°C (boiling point $_{0.1}$: 140°–144°C).

1a. 185g of 3-methoxy-4-hydroxybenzyl alcohol are dissolved in 1,250 ml of DMSO and 35g of anhydrous hydrocyanic acid are passed in over the course of 1 hour at 125°C. The mixture is then stirred for a further 2 hours, and worked up as indicated above. The yield was 160.5g (82% of theory).

EXAMPLE 2

2-Hydroxyphenylacetonitrile

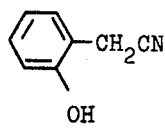

29.8g of 2-hydroxybenzyl alcohol are dissolved in 250 ml of dimethylsulfoxide, together with 18g of potassium cyanide, and the mixture is heated to 125°C. 16g of glacial acetic acid are then added dropwise over the course of 1 hour and the mixture is stirred for a further 2 hours at 125°C. The dimethylsulfoxide is removed in vacuo and the residue is stirred with 200 ml of water and 150 ml of chloroform. The chloroform phase is separated off and the aqueous phase is re-extracted with 150 ml of chloroform. The combined chloroform phases are extracted by shaking with water and dried with sodium sulfate. After distilling off the chloroform, an oil remains, which solidifies on cooling. Yield: 19.8g = 60.5% of theory. Recrystallization from benzene/ligroin: melting point 118°C.

EXAMPLE 3

4-Hydroxyphenylacetonitrile

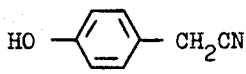

Analogously to the above example, 29.8g of 4-hydroxybenzyl alcohol gave 17.2g (54% of theory) of 4-hydroxyphenylacetonitrile of melting point 58°–59°C.

EXAMPLE 4

Analogously to the procedure described in Example 1, the following compounds are prepared:

3,5-dimethyl-4-hydroxybenzyl alcohol gave 3,5-dimethyl-4-hydroxyphenylacetonitrile, m.p. 76°C, 62% yield.

5-methyl-2-hydroxybenzyl alcohol gave 5-methyl-2-hydroxyphenylacetonitrile, m.p. 104° to 106°C, 52% yield.

2,6-dimethyl-4-hydroxybenzyl alcohol gave 2,6-dimethyl-4-hydroxyphenylacetonitrile, m.p. 146°C, 51% yield.

5-methoxy-2-hydroxybenzyl alcohol gave 5-methoxy-2-hydroxyphenylacetonitrile, m.p. 109°–110°C, 65% yield, and 3,5-dimethoxy-4-hydroxybenzyl alcohol gave 3,5-dimethoxyhydroxyphenylacetonitrile, b.p. 140°–142°C/0.02, 81% yield.

What is claimed is:

1. Process for the preparation of an ortho or parahydroxyphenylacetonitrile of the formula:

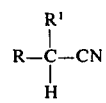

wherein
R is ortho or parahydroxyphenyl, further unsubstituted or further substituted by one or two substituents independently selected from the group consisting of lower alkyl or lower alkoxy and
R$^1$ is hydrogen, lower alkyl, phenyl or carbon (lower alkoxy), which comprises allowing the corresponding ortho or parahydroxybenzyl alcohol of the formula:

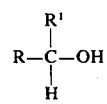

to react with hydrogen cyanide in the presence of a diluent at a temperature of from about 80° to about 190°C.

2. The process according to claim 1 wherein the temperature is from about 110° to about 140°C.

3. The process according to claim 1 wherein the hydrogen cyanide is generated in situ.

4. The process according to claim 1 wherein the diluent is water.

5. The process according to claim 1 wherein the diluent is an inert organic solvent.

6. The process according to claim 1 wherein R' is hydrogen.

7. The process according to claim 6 wherein R is 3-methoxy-4-hydroxyphenyl.

8. The process according to claim 6 wherein R is 2-hydroxyphenyl.

9. The process according to claim 6 wherein R is 4-hydroxyphenyl.

10. The process according to claim 1 wherein 3-methoxy-4-hydroxybenzyl alcohol is allowed to react with hydrogen cyanide in an inert organic solvent at temperatures of from about 110° to about 140°C.

11. The process according to claim 10 wherein the hydrogen cyanide is generated in situ from the reaction of an alkali metal cyanide and an acid.

12. The process according to claim 10 wherein the inert organic solvent is a polar aprotic solvent.

13. The process according to claim 12 wherein the solvent is dimethylsulfoxide.

* * * * *